United States Patent
Briggs et al.

(10) Patent No.: US 12,228,500 B2
(45) Date of Patent: Feb. 18, 2025

(54) INFRARED ABSORPTION-BASED COMPOSITION SENSOR FOR FLUID MIXTURES

(71) Applicant: CALIFORNIA INSTITUTE OF TECHNOLOGY, Pasadena, CA (US)

(72) Inventors: Ryan M. Briggs, Pasadena, CA (US); Linda Y. Del Castillo, Pasadena, CA (US); Mina Rais-Zadeh, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 203 days.

(21) Appl. No.: 17/758,796

(22) PCT Filed: Feb. 23, 2021

(86) PCT No.: PCT/US2021/019227
§ 371 (c)(1),
(2) Date: Jul. 13, 2022

(87) PCT Pub. No.: WO2021/173547
PCT Pub. Date: Sep. 2, 2021

(65) Prior Publication Data
US 2023/0041370 A1    Feb. 9, 2023

Related U.S. Application Data

(60) Provisional application No. 62/980,836, filed on Feb. 24, 2020.

(51) Int. Cl.
*G01N 21/31* (2006.01)
*E21B 47/01* (2012.01)
*G01N 21/359* (2014.01)

(52) U.S. Cl.
CPC ......... *G01N 21/3151* (2013.01); *E21B 47/01* (2013.01); *G01N 21/359* (2013.01); *G01N 2201/0218* (2013.01)

(58) Field of Classification Search
CPC ............. G01N 21/3151; G01N 21/359; G01N 33/1833; G01N 33/1886;
(Continued)

(56) References Cited

U.S. PATENT DOCUMENTS 4,394,573 A * 7/1983 Correa ..................... G01V 8/02
250/573
8,461,519 B2   6/2013 Lievois et al.
(Continued)

FOREIGN PATENT DOCUMENTS

EP    3570008 A1    11/2019
JP    2006087764 A *  4/2006
JP    2012052880 A    3/2012

OTHER PUBLICATIONS https://web.archive.org/web/20200804023248/https://www.ld-pd.com/?a=cp3&id=274 Wayback archive of website from Aug. 2020 (Year: 2020).*

(Continued)

*Primary Examiner* — Uzma Alam
*Assistant Examiner* — Jonathon Cook
(74) *Attorney, Agent, or Firm* — Steinfl + Bruno LLP

(57) ABSTRACT

A composition sensor for measuring composition of fluid mixtures is presented. The composition sensor includes a plurality of high-brightness emission sources having respective spectrally narrow wavelength emission bands in the infrared region. The wavelength emission bands overlap absorption wavelength bands of the composition. The wavelength emission bands are wavelength multiplexed and time multiplexed prior to emission through a fluid mixture. A (Continued)

single optical detector senses the emitted light. The composition sensor includes arms that can rotate to measure composition at different angular position of a pipe in a lateral section of an oil well. Rotation of the arms is provided by rotation of an element of a mobile vessel to which the arm is rigidly coupled. The rotation of the arms is provided by a rotation of a nose of the mobile vessel that rotates independently from a main body of the mobile vessel.

20 Claims, 13 Drawing Sheets

(58) Field of Classification Search
CPC ............. G01N 2201/0218; E21B 47/01; G01J 3/0202; G01J 3/0294; G01J 3/32
See application file for complete search history.

(56) References Cited

U.S. PATENT DOCUMENTS

| | | | |
|---|---|---|---|
| 2004/0201835 A1 | 10/2004 | Coates et al. | |
| 2014/0226149 A1* | 8/2014 | Coates | G01N 21/31 356/51 |
| 2018/0266131 A1* | 9/2018 | Witelson | G01N 33/1826 |
| 2019/0084658 A1* | 3/2019 | Bonel | B63G 8/001 |
| 2019/0391014 A1* | 12/2019 | Stevenson | G01N 21/25 |
| 2021/0040702 A1* | 2/2021 | Sehsah | G01N 33/241 |
| 2022/0364947 A1* | 11/2022 | Speck | G01S 17/89 |

OTHER PUBLICATIONS

A guide to oil in water monitoring for environmental compliance, Arjay engineering, 2014, https://www.arjayeng.com/wp-content/uploads/Guide-to-Oil-in-Water-Monitoring.pdf (Year: 2014).*

LD-DP inc https://web.archive.org/web/20200804023248/https://www.ld-pd.com/?a=cp3&id=274 Wayback archive of website from Aug. 2020 (Year: 2020).*

Anonymous: 11 Exalos SLED Products, Feb. 7, 2020, pp. 1-1, XP055802528, 3 Pages. Retrieved from the Internet: URL: https://web.archive.org/web/20200207083940/http://www.exalos.com/sledproducts/.

International Search Report and Written Opinion issued for International PCT Application No. PCT/US2021/019227 Filed On Feb. 23, 2021, on behalf of California Institute of Technology. Mail Date: Jul. 12, 2021. 22 Pages.

* cited by examiner

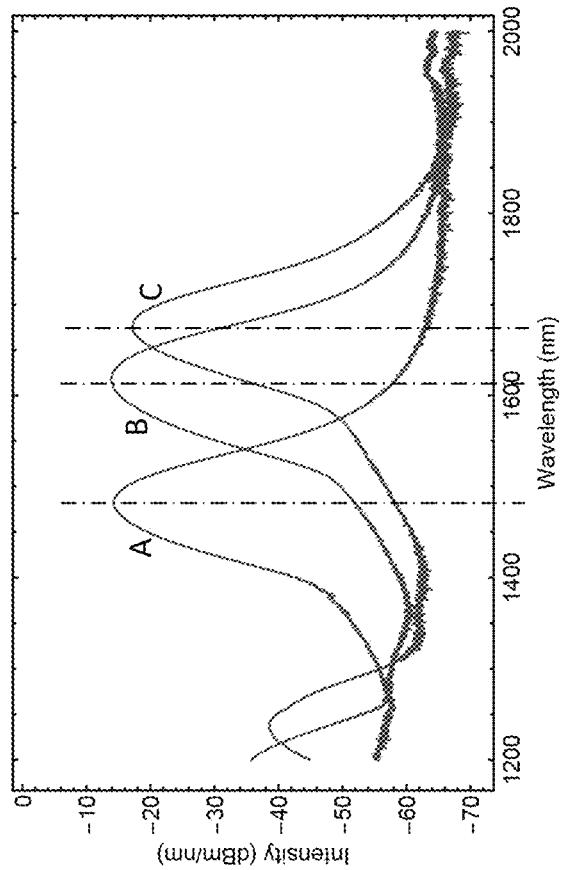
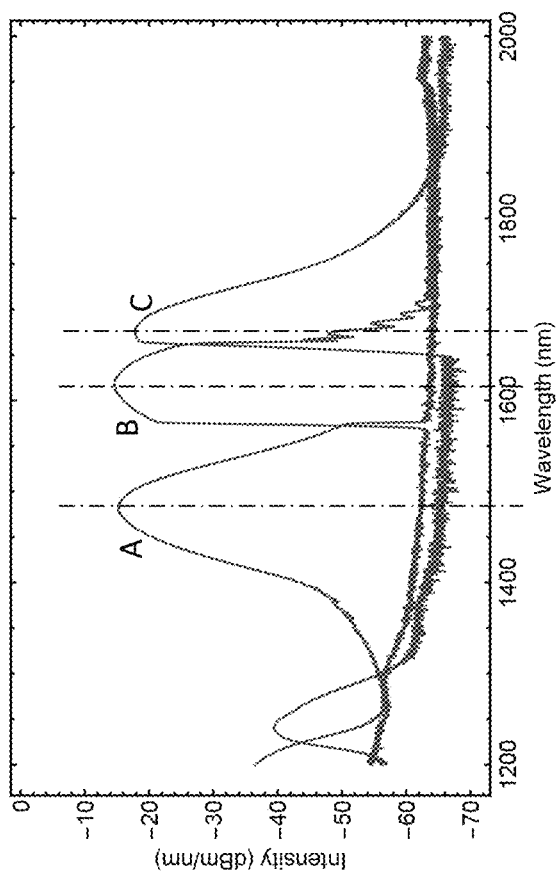

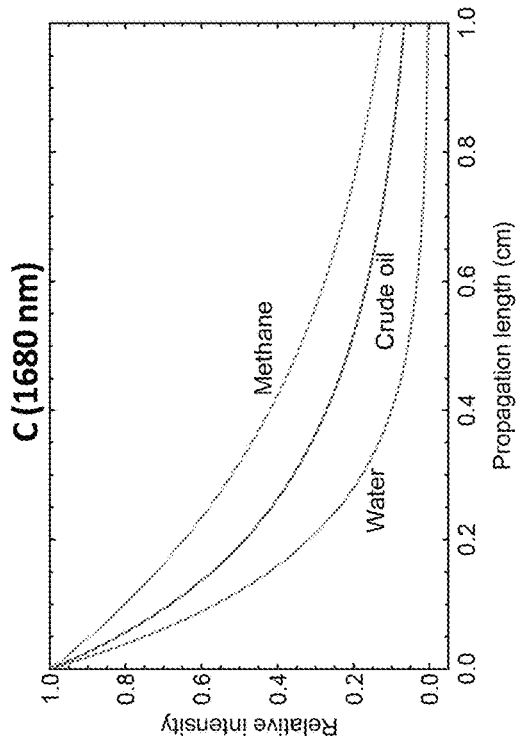
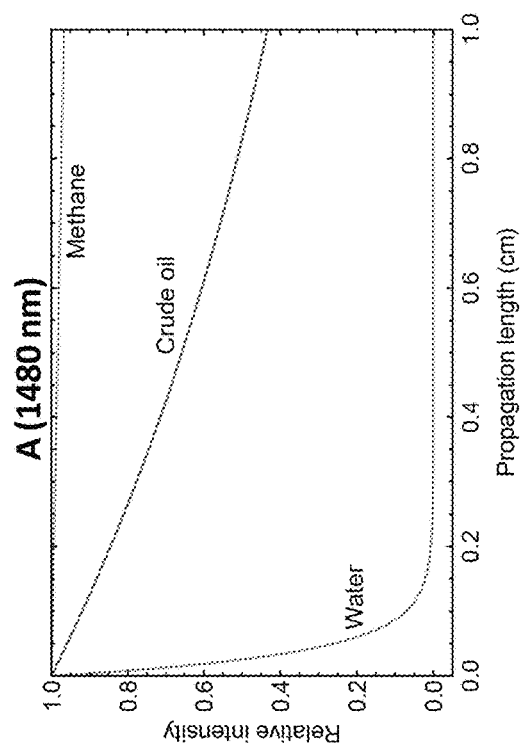
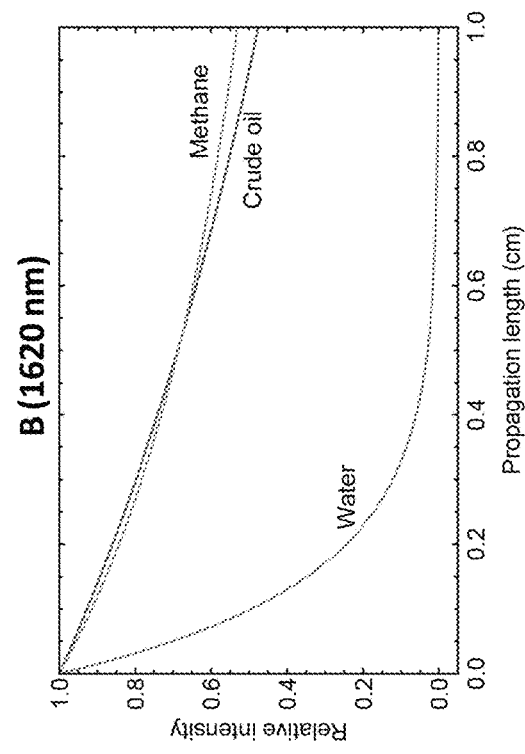
FIG. 8A
FIG. 8B
FIG. 8C

INFRARED ABSORPTION-BASED COMPOSITION SENSOR FOR FLUID MIXTURES

CROSS REFERENCE TO RELATED APPLICATIONS

The present application is the U.S. National Stage of International Patent Application No. PCT/US2021/019227 filed on Feb. 23, 2021 which, in turn, claims priority to and the benefit of U.S. provisional patent application Ser. No. 62/980,836 entitled "Infrared Absorption-Based Composition Sensor for Liquid-Phase Mixtures", filed on Feb. 24, 2020, the disclosure of which is incorporated herein by reference in its entirety.

STATEMENT REGARDING FEDERALLY SPONSORED RESEARCH OR DEVELOPMENT

This invention was made with government support under Grant Number 80NMO0018D0004, awarded by NASA (JPL). The government has certain rights in the invention.

TECHNICAL FIELD

The present disclosure generally relates to systems and methods for measuring composition of fluid mixtures, such as, for example, oil, water, and gas composition of an oil well.

BACKGROUND

Detailed information about physical properties (e.g., reservoir inflow) in the downhole of an oil-gas producing well, is important to help optimize production and field development. Inflow data points such as oil-gas-water relative concentrations, flow rates, pressure, and temperature, for example, are key to understanding the nature of the reservoir properties and the effect of well drilling and completion methods. Although useful, the inflow data are not often measured in real-time, or with considerable frequency (weekly or more frequently), along the lateral section of the well due to technical or cost-prohibitive challenges. Instead, surface well-head production data (total flow rates, pressure, temperature, composition, etc.) are measured for well performance diagnostics and for reporting purposes.

Attempts to instrument the well for real time or at least weekly measurements with continuous electrical or fiber optic cables for powering sensors to measure and deliver physical properties in the downhole of a well have been tested and have not been cost effective. This is particularly true for shale and tight development wells that have, for example, long laterals and multiple perforation entry points of their casing pipe (to contact the rock formation) which then undergo high-pressure hydraulic fracturing to increase hydrocarbon inflows from oil-bearing rock formations. Such harsh activities can easily damage not only the sensors but also power and data cables in the downhole of a well.

Production-logging tools (PLTs) are used routinely within long, horizontal wells to make measurements of local pressure, temperature, composition (e.g., relative concentrations) and flow rates. PLTs, however, are provided as a service and require well intervention for data to be collected; the operational cost and complexity limiting the frequency the data can be collected within a well.

Unconventional tight rock geologic formations may require a large number of oil/gas wells (holes) drilled in close proximity to each other to effectively extract the hydrocarbon contained in a field. Horizontally-drilled wells may be used in these applications since the hydrocarbon-bearing rock formations tend to exist in stratified layers aligned perpendicular to the gravity vector.

The typical vertical section of these wells can be 1-3 km below the surface and can extend laterally (e.g., in a generally horizontal direction) for distances of, for example, 2-3 km or even more. Oil, natural gas, and water may enter the well at many locations (production intervals/zones open to perforations and fracturing) formed along a lateral distance (e.g., 2-3 km or more) of the well with local flow rates and composition (e.g. oil/water fractions or relative concentrations) varying due to inherent geology and the accuracy with which the well intersects (e.g., at the production intervals or sections) the oil-bearing rock formations. In general, information about the performance or hydrocarbon delivery and capacity of a well, such as, for example, flow rate, pressure, and composition, can practically be measured at the surface of the well as-combined values and with little or no knowledge of individual contributions from each of the production intervals or zones. Lack of local information of the inflow details of the well, at, for example, the production intervals or zones, can be a barrier to improving the efficiency of oil-gas extraction from the overall field.

Better knowledge of local interval inflow data across each or multiple entry points (e.g. physical properties such as flow rates, pressure, temperature, composition, etc.) at the downhole of a well (e.g., along the horizontal/lateral section of the well) may help in making better decisions about placement of subsequent perforation/completion intervals for production in a well and/or subsequent drilling of other wells in the field.

For example, an oil production field may have a variety of drilled wells, including an unconventional horizontal oil well that extracts oil from shale and tight formation through a plurality of production intervals or zones (shown as rectangles). In order to develop the field, producing the hydrocarbon-bearing rock formations, a number of wells (i.e., holes) may be drilled and spaced, for example, on the order of 500 feet apart from each other. These wells are drilled and completed serially so that information may be gathered from a downhole of a first well, for example, and can aid in determining where to perforate the casing and to apply hydraulic fracturing at selected intervals of the formation in a second and following well.

SUMMARY

Although the present systems and methods are described with reference to oil-gas-water mixtures found in oil wells, such systems and methods may equally apply to any other fluid mixtures containing unique components with separate wavelength absorption bands.

According to one embodiment the present disclosure, a system for gathering information about physical properties in a lateral section of a well is presented, the system comprising: a mobile vessel configured for submersion in the lateral section of the well; and a composition sensor attached to the mobile vessel, the composition sensor comprising: a pair of opposing arms separated by a distance that defines a length of a measurement flow channel of the composition sensor; an emission aperture and a collection aperture oppositely arranged in the pair of opposing arms; and a plurality of spectrally narrow emission sources having respective plurality of emission wavelength bands in an infrared wavelength region between 1400 nm to 1800 nm, wherein the composition sensor is configured to emit the plurality of emission wavelength bands through the emission aperture according to a time multiplexing scheme.

According to a second embodiment of the present disclosure, an infrared absorption-based composition sensor is presented, the sensor comprising: a pair of opposing arms separated by a distance that defines a length of a measurement flow channel of the composition sensor; an emission aperture and a collection aperture oppositely arranged in the pair of opposing arms; a plurality of spectrally narrow emission sources having respective plurality of emission wavelength bands in a near infrared wavelength region; and a wavelength multiplexer configured to couple the plurality of emission wavelength bands into a single optical fiber for emission through the emission aperture, wherein the composition sensor is configured to emit the plurality of emission wavelength bands through the emission aperture according to a time multiplexing scheme.

According to a third embodiment of the present disclosure, a method for measuring composition of a fluid mixture in a downhole of an oil well, the method comprising: oppositely arranging an emission aperture and a collection aperture in the fluid mixture at a distance between 1 mm and 10 mm; coupling a plurality of spectrally narrow emission sources having respective plurality of emission wavelength bands in an infrared wavelength region between 1400 nm to 1800 to a single optical fiber through a wavelength multiplexer; emitting the plurality of emission wavelength bands through the single optical fiber and through the emission aperture according to a time multiplexing scheme; based on the emitting, for each of the plurality of emission wavelength bands, sensing a time multiplexed emitted wavelength band collected through the collection aperture; based on the sensing, determining relative absorptions of components of the fluid mixture at each of the plurality of emission wavelength bands; and based on the determining, measuring relative concentrations of each of the components of the fluid mixture, thereby measuring the composition of the fluid mixture.

Further aspects of the disclosure are shown in the specification, drawings and claims of the present application.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

Figure 6A:
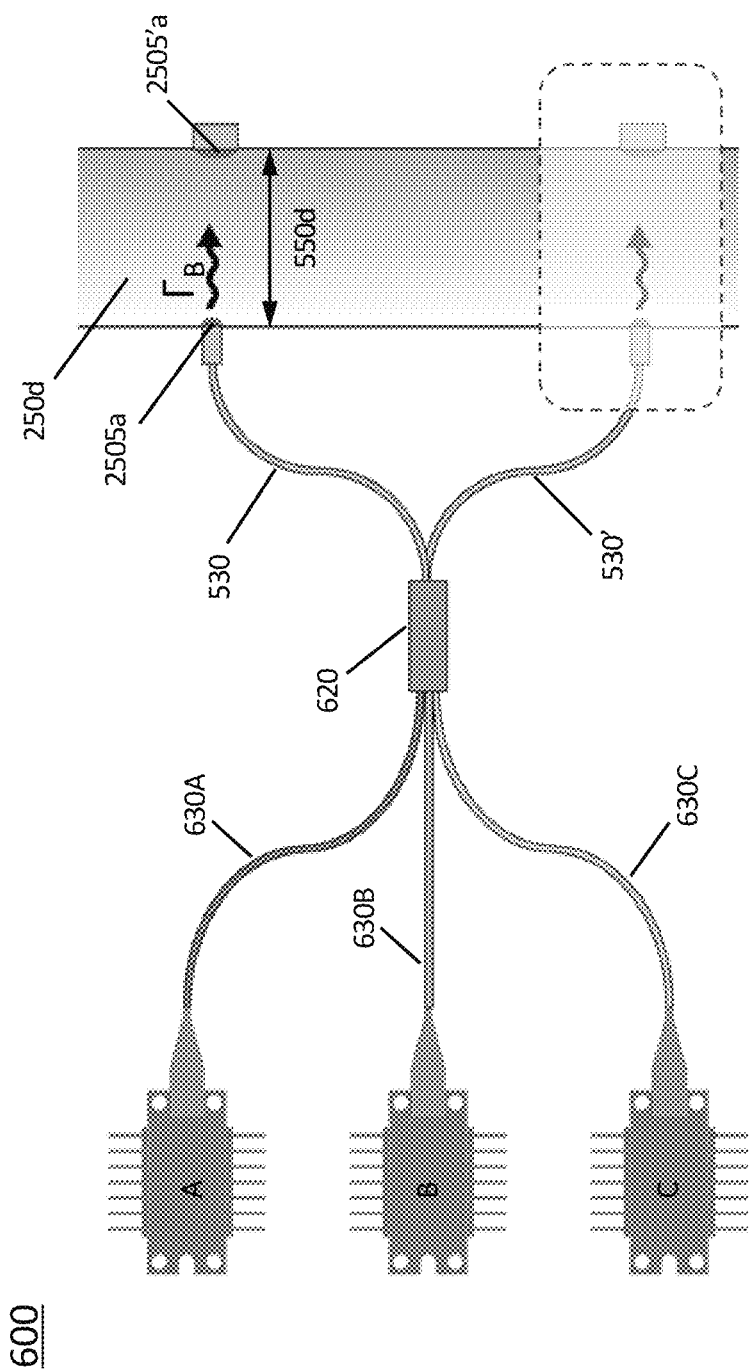
FIG. 6A shows an optical layout of the composition sensor according to the present disclosure.

6C show graphs representative of emission spectra of the SLEDs of FIG. 6B through the wavelength multiplexer of FIG. 6A.

Figure 6D:
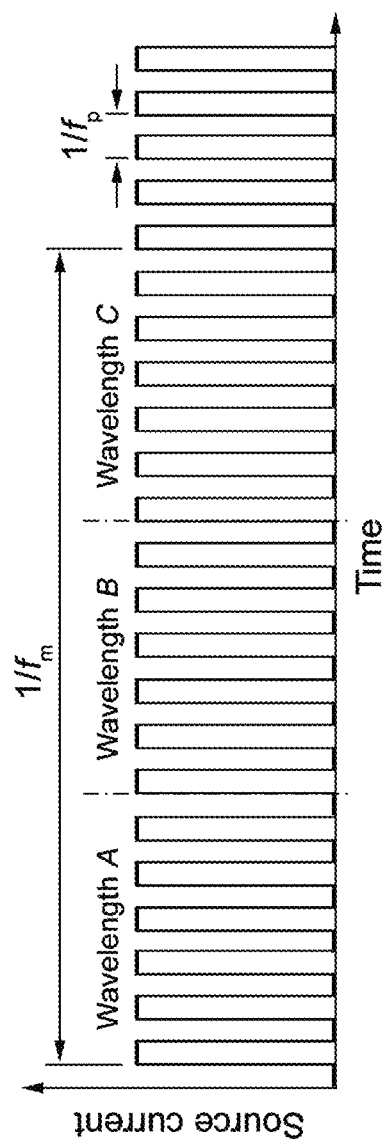
FIG. 6B show graphs representative of emission spectra of exemplary superluminescent light emitting diodes (SLEDs) used in the composition sensor according to the present disclosure.

FIG. 6D shows a graph representative of a time multiplexing scheme of the SLEDs used in the composition sensor according to the present disclosure.

Figure 7A:
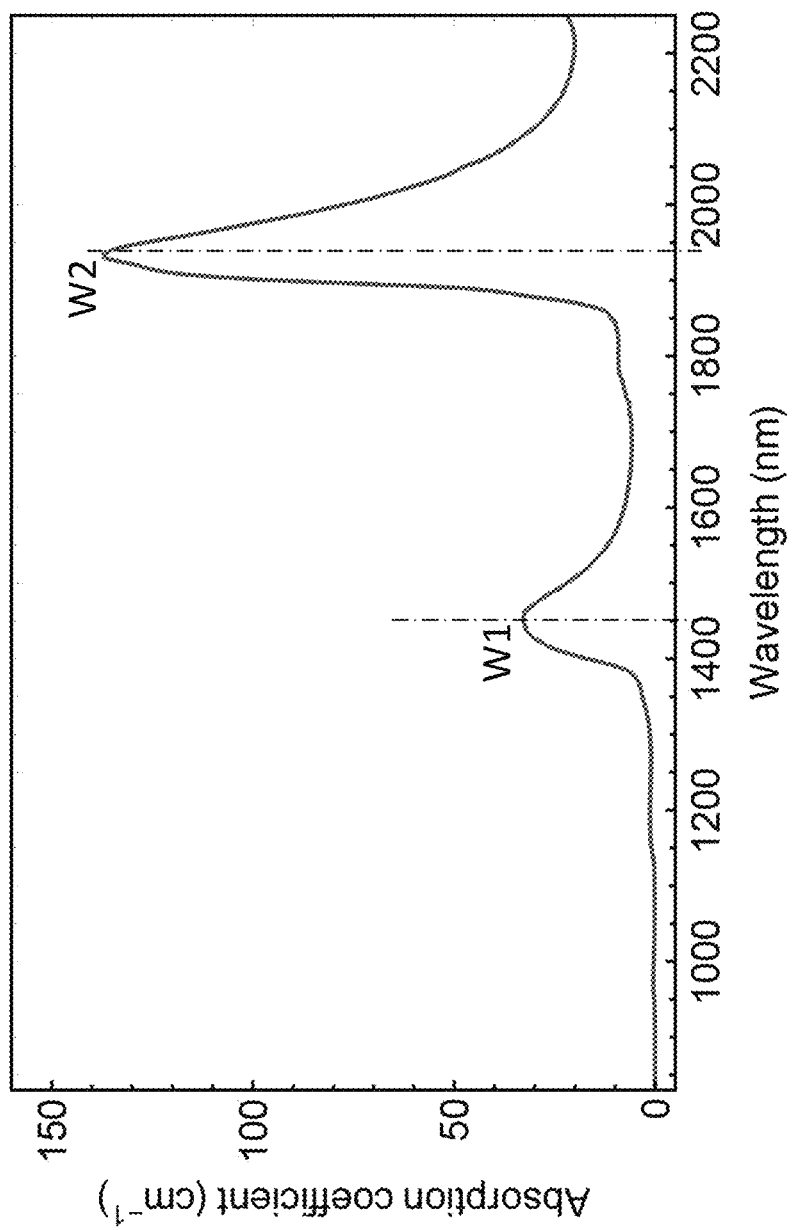

FIG. 7A shows a graph representative of a wavelength absorption bands of water.

Figure 7B:
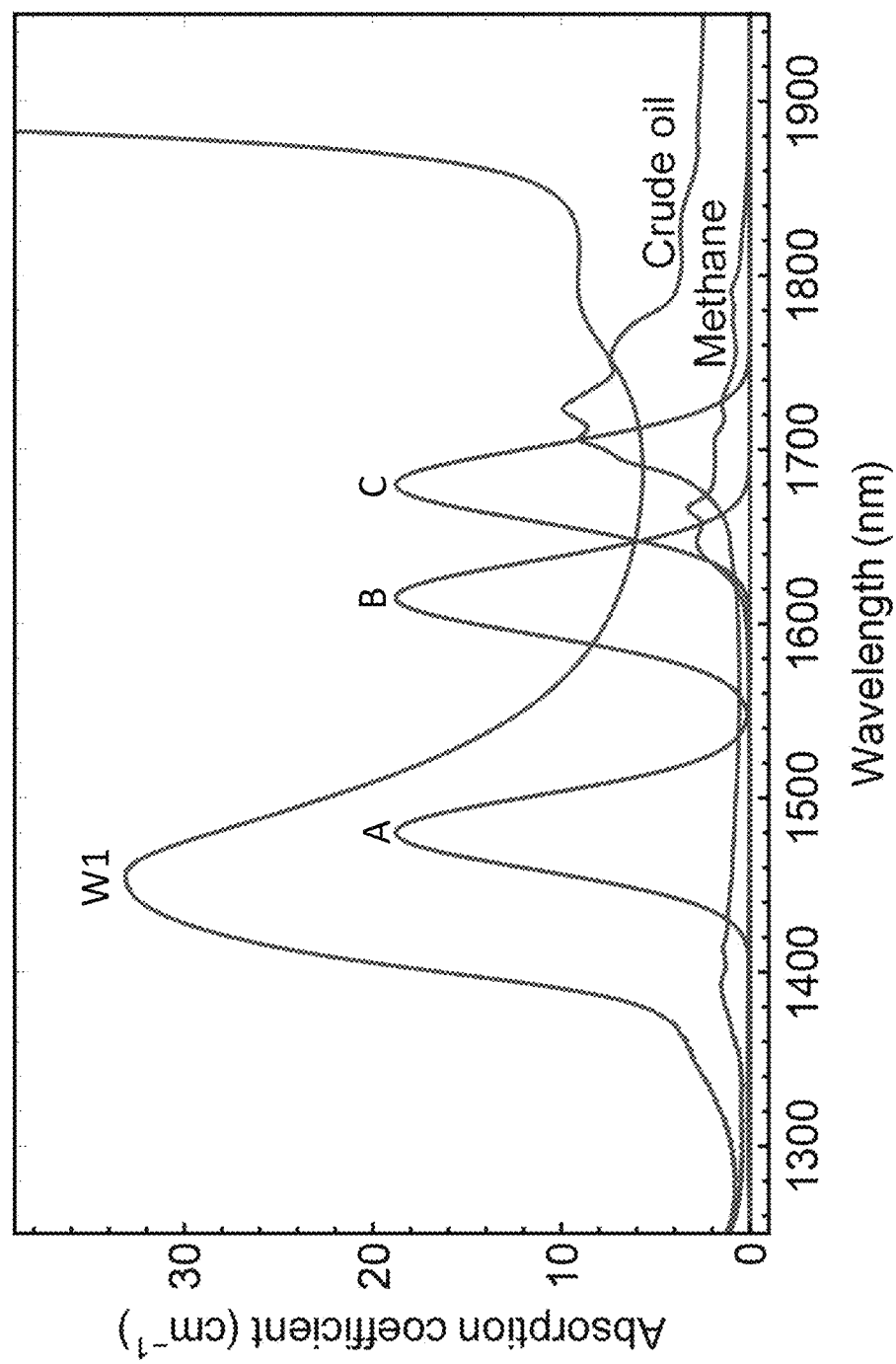

FIG. 7B show graphs representative of wavelength emission bands of the composition sensor according to the present disclosure, and wavelength absorption bands of components of an oil well mixture.

FIGS. 8A, 8B and 8C show graphs representative of emission attenuation at different wavelengths through components of an oil well mixture as a function of a propagation channel length.

Figure 9:
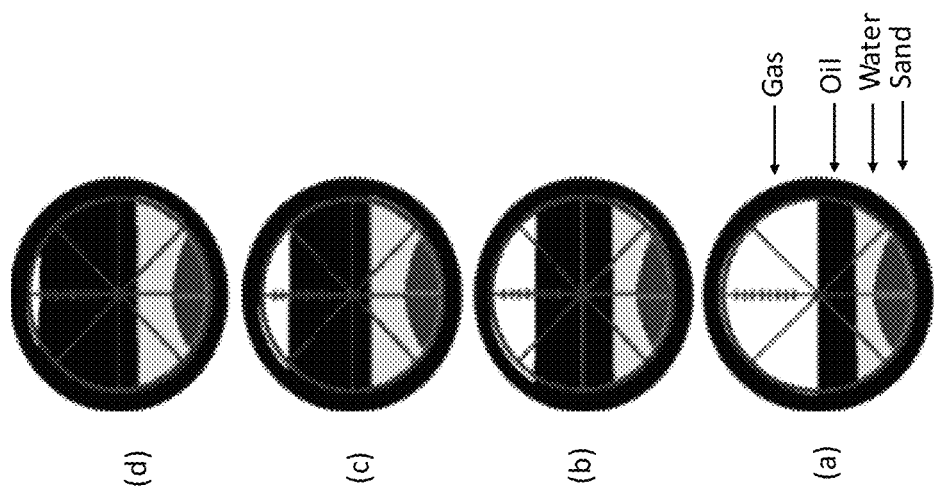

FIG. 9 show stratified components of a pipe in a lateral section of an oil well mixture for different flow conditions of the mixture.

DEFINITIONS

As used herein the term "flow velocity" of a fluid may refer to the motion of the fluid per unit of time and may be represented locally by a corresponding "fluid velocity vector". As used herein, the term "flow rate" of a fluid may refer to a volume of the fluid flowing past a point per unit of time. Therefore, considering a cross-sectional area of a flow of fluid, such as a flow of fluid through a lateral section of an oil well, the flow rate through the cross-sectional area can be provided by the flow velocity at that area.

As used herein the term "infrared", "infrared light" and "infrared emission" are synonymous and may refer to an electromagnetic radiation (EMR) with wavelengths in a range from about 780 nanometers to 1 millimeter and longer than those of visible light. As used herein the term "near infrared", "near infrared light" and "near infrared emission" are synonymous and may refer to an electromagnetic radiation (EMR) with wavelengths in a range from about 780 nanometers to 3,000 nanometers.

DETAILED DESCRIPTION

As set forth above, information may be gathered from a downhole of a first well, for example, and can aid in determining where to perforate the casing and to apply hydraulic fracturing at selected intervals of the formation in a second and following well. Other useful information that may be collected within a well includes, by way of non-limiting example, fluid mixture composition, as provided for example, by relative concentrations of one or more of oil, water and gas. It is understood that a fluid may include different phases in dependence of different thermodynamic conditions, the different phases including a liquid phase and a gaseous phase.

Certain prior art sensors for measuring composition of fluid mixtures from an oil well are based on a single spectrally broad emission source (e.g., emitter, broader than 100 nm) that encompasses multiple spectrally separated wavelength absorption bands of components of the mixtures. In order to resolve transmission of the emitted light through the different wavelength absorption bands, such prior art sensors must send light transmitted through a sample being analyzed to different (spectral) bandpass filters for detection at corresponding optical detectors (e.g., photodetectors). In one such prior art, spatially separated optical fibers are used to separate light that is subsequently passed through the different bandpass filters. Such prior art sensors may require the fluid mixture being analyzed to be at "typical test line pressures," where the absorption from gaseous components (e.g., gas, methane) of the mixture in the 1000 to 2000 nm wavelength range is negligible compared to the absorption of liquid components (e.g., water and/or oil). Furthermore, such prior art sensors are designed to operate outside of a well and include fixtures designed to precondition the fluid mixture prior to analysis, such as, for example, separators to separate/remove gaseous components from the mixture, and mixers to provide a sufficiently homogeneous liquid mixture.

Some shortcomings of the prior art composition sensors include: i) wasted power due to emitted optical power that is rejected outside the filter passbands, the filter passbands being significantly spectrally narrower than the emission source; ii) longer integration times, and therefore slower measurement times, as a consequence of relatively lower signal-to-noise ratios at the optical detectors; iii) lower spatial accuracy as a consequence of usage of the spatially separated optical fibers which due to their relatively large cross sectional areas (e.g., fiber diameters on the order of 0.1 to 1 mm) may not resolve spatial variations in the fluid mixture (thereby requirement for a preconditioning mixer); and iv) inability to measure/operate in the presence of gaseous components (thereby requiring operation at a relatively low "typical test line pressures" and/or usage of a preconditioning separator).

Teachings according to the present disclosure solve the prior art shortcomings by providing an infrared absorption-based composition sensor that is operable in a downhole of an oil well. Accordingly, the composition sensor according to the present teachings may measure relative concentrations of oil, gas and water in a fluid mixture of the downhole under a wide range of thermodynamic conditions, including at downhole pressures greater than 1000 psi, accurately and efficiently. Furthermore, the composition sensor according to the present disclosure may be integrated on a mobile vessel for measuring downhole composition profiles for extended periods of time and unattended.

Figure 1:
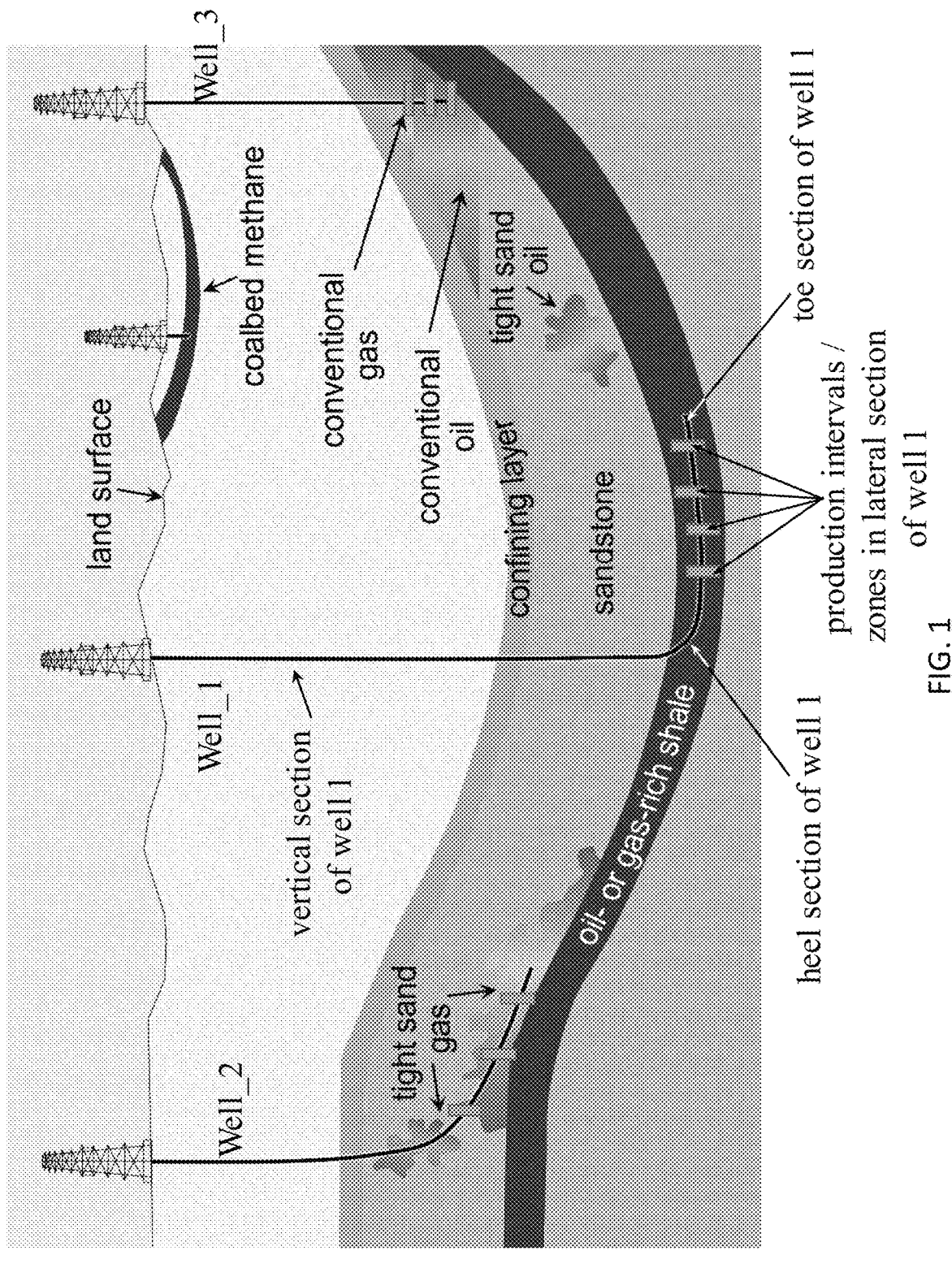
FIG. 1 illustrates a cross sectional view of an exemplary known oil production field, comprising one or more drilled wells for production of oil and/or gas in which a mobile vessel comprising a composition sensor constructed in accordance with this disclosure may be disposed.

The mobile vessel described herein may be used in a number of settings, an example of which is depicted in FIG. 1, which illustrates a cross sectional view of an exemplary oil production field (100), comprising one or more drilled wells (Well_1, Well_2, . . . ) for production and extraction of oil and/or gas from various regions of the field. In particular, as can be seen in FIG. 1, a vertical section of the Well_1 may be drilled to reach and penetrate an oil- or gas-rich shale (e.g., rock formation), and a lateral (e.g., horizontal) section of the Well_1, which, in the exemplary case of FIG. 1 is substantially horizontal, may be drilled along the shale, starting from a heel section of the Well_1, and ending at a toe section of the Well_1. Generally, the vertical section of the Well_1 may extend 1 to 3 km below the surface and the lateral section of the Well_1 may extend for distances of, for example, 2-3 km or more.

With continued reference to FIG. 1, fluids, including oil, water, and natural gas, may enter the Well_1, for example, through open-hole or a casing of the Well_1, at production perforated intervals/zones that may be formed in the lateral section of the Well_1. Each of such production intervals/zones may include holes and/or openings that extract the fluid from the shale and route into the casing of the Well_1. As shown in FIG. 1, the perforated intervals/production zones may be separated by distances of, for example, about 100 meters (i.e., about 300 feet), and between each of the intervals (or stages) there are several clusters of perforations with closer spacing in order to cover a lengthy lateral and extract more hydrocarbon from shale/tight formations. Since there are many production zones, the inflow contribution for each of the intervals (or zones or clusters), such as, for example, local pressure, temperature, flow rates, and composition, may vary due to inherent geology and the accuracy with which the lateral section of the Well_1 intersects the oil-bearing rock formations at the production zones.

As described above, collecting data at regions of the Well_1, for example, close to each of the production zones, can help evaluate effectiveness of inflow contribution for each of the production zones and further help in optimizing production (e.g. by altering the perforation/completion design). The composition sensor according to the present disclosure, integrated with a mobile vessel as described herein, may be used to measure relative concentrations of oil, water and gas of the fluid (mixture) in the lateral section of the Well_1, the relative concentrations inferred by emission absorptions at selected and separate emission wavelength bands (e.g., FIGS. 6B, 6C, 7A, 7B later described) provided by separate emitters of the composition sensor. Because the emission absorption may be a function of local thermodynamic conditions (e.g., temperature), mapping of the emission absorptions to relative concentrations of components of the fluid mixture may be in view of data sensed by other sensors that are placed inside of the lateral section of the well. Data sensed by such other sensors may include data related to, for example, temperature, pressure, and fluid velocity.

Figure 2:
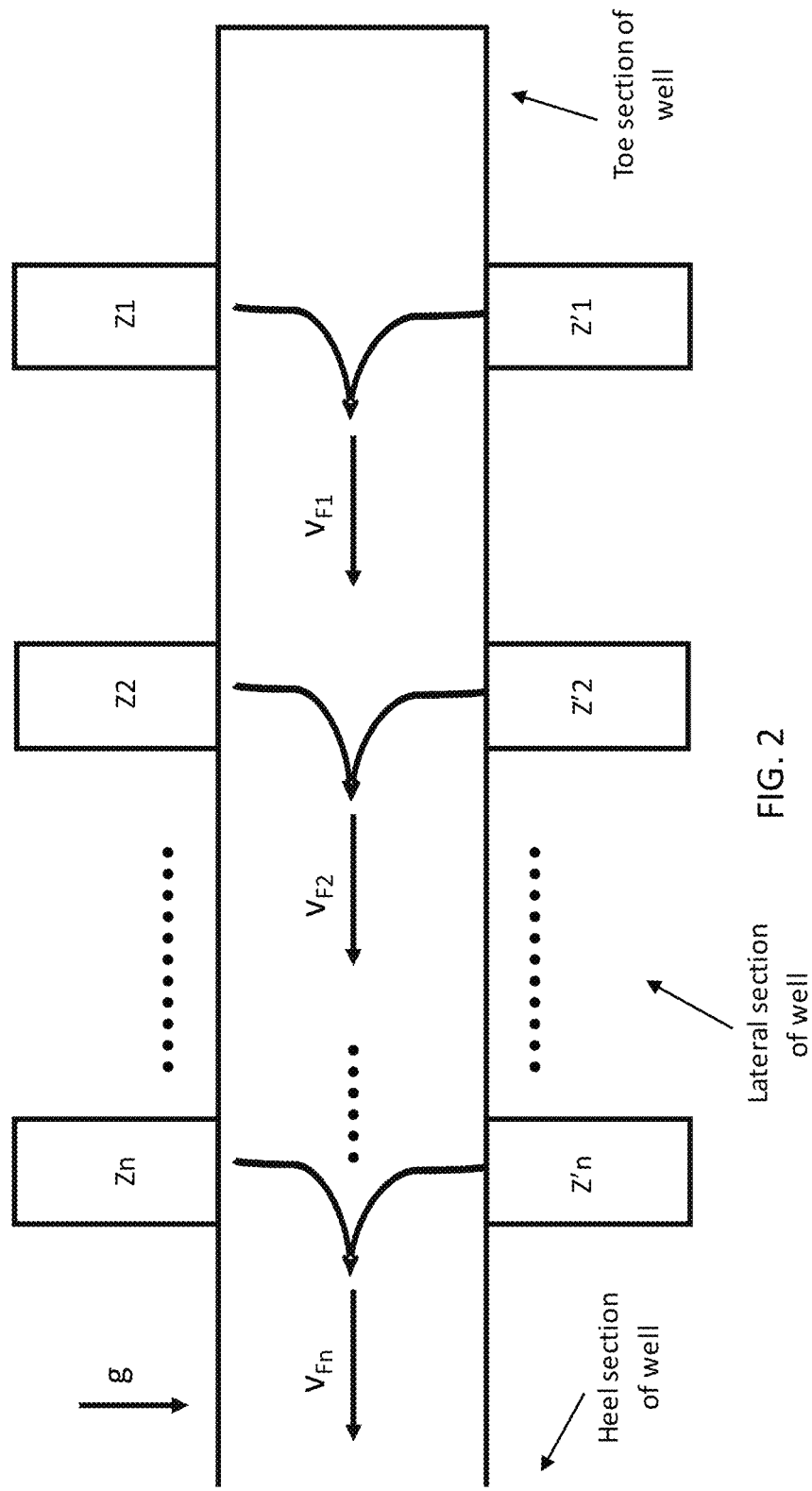
FIG. 2 shows a lateral section of a well of the oil production field shown in FIG. 1 comprising a plurality of production zones in which a mobile vessel comprising a composition sensor constructed in accordance with this disclosure may be disposed.

FIG. 2 shows a lateral section of a well of the oil production field shown in FIG. 1 comprising a plurality of production zones indicated as (Z1, Z'1, . . . , Zn, Z'n). Also shown in FIG. 2 are local fluid velocity vectors ($V_{F1}, \ldots, V_{Fn}$) at vicinity of respective production zones. For example, the fluid velocity vector $V_{F1}$, may be considered solely based on an inflow (of fluid) contribution by the last production zone (Z1, Z'1) close to the toe section of the well. On the other hand, the fluid velocity vector $V_{F2}$ may be considered based on a combination of the inflow contribution of the production zone (Z2, Z'2) combined with the inflow contribution of the last production zone (Z1, Z'1). A performance of each of the production zones (Z1, Z'1, . . . , Zn, Z'n) based on a corresponding inflow contribution may be assessed by measuring a relative concentration of fluid mixtures before and after each production zone.

Figure 3:
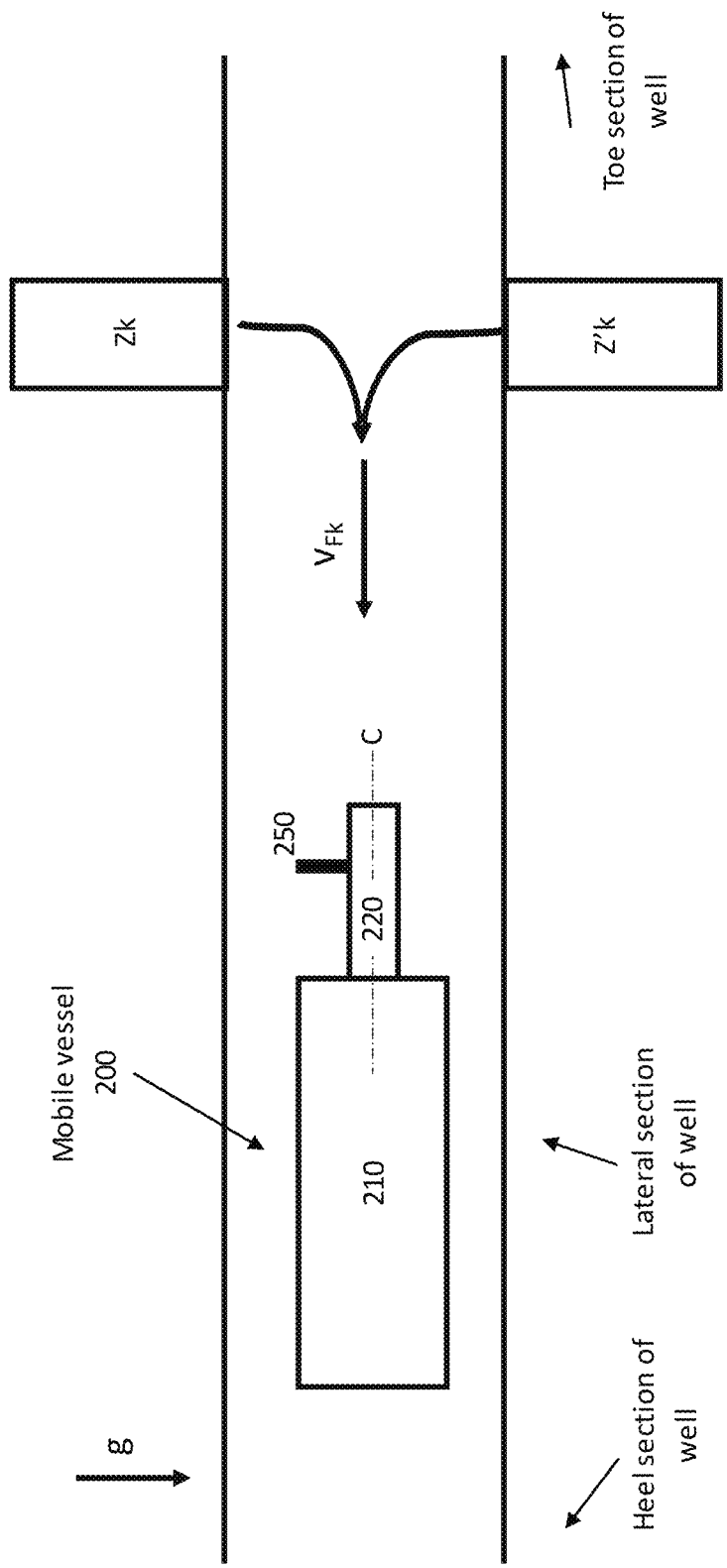
FIG. 3 shows an exemplary embodiment of a mobile vessel comprising a composition sensor according to the present disclosure, the mobile vessel positioned in a lateral section of a well of the oil production field shown in FIG. 1.

When fitted in a mobile vessel, such as a mobile robot, the composition sensor according to the present disclosure may be used to measure relative concentrations of oil, water and gas provided by each of the production zones (Z1, Z'1, . . . , Zn, Z'n). This is shown in FIG. 3, where the mobile vessel (200), including for example an element (210) and an element (220), fitted with the composition sensor (250) according to the present teachings is positioned downstream (e.g., towards the heel section of the well) of the production zone (Zk, Z'k) for measurement of a performance of the production zone. In this case, the mobile vessel (200) may be controlled to remain stationary during the gathering/sensing of corresponding measurement data, and move to a next production zone for a next measurement. In some embodiments, actual derivation of the relative concentrations of the fluid mixtures may be performed either in real-time or non-real-time based on data sensed by the composition sensor (250) which may be combined with data sensed by other sensors as described above. It should be noted that the term "data" as used herein may relate to an ensemble of data values representative of signals gathered/sensed by one or more sensors of, for example, the composition sensor of the present teachings. Such data may be stored on local or remote memory for immediate or future use.

Figure 4B:
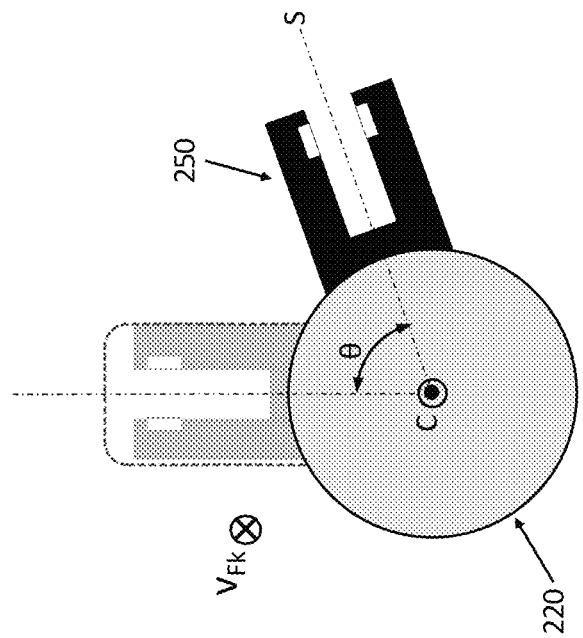
FIG. 4B shows a front view of the mobile vessel of FIG. 3 with the composition sensor positioned at a second angular position.
Figure 4A:
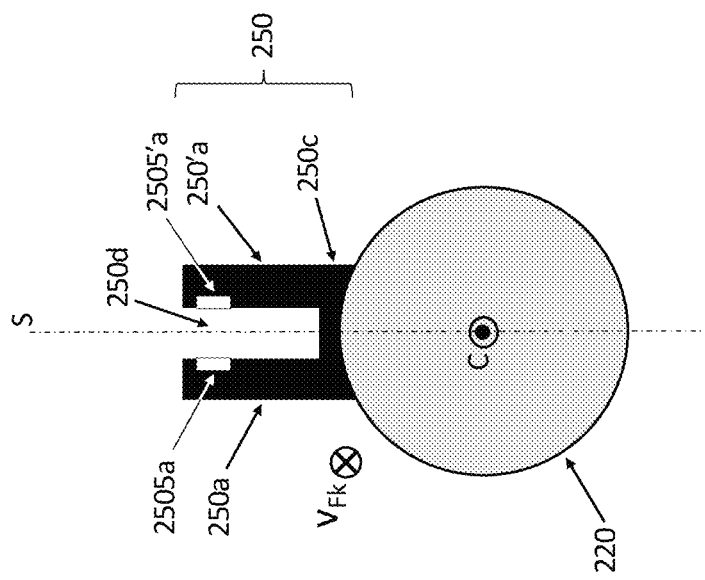
FIG. 4A shows a front view of the mobile vessel of FIG. 3 with the composition sensor positioned at a first angular position.

FIG. 4A shows a front view of the vessel of FIG. 3 with the composition sensor (250) positioned at a first angular position about a center axis, C, of the element (220, e.g., nose) of the mobile vessel (200) shown in FIG. 3. The center axis C may be a common axis of the elements (210) and (220) of the mobile vessel (200), or may be an axis that is different from (e.g., parallel to) a center axis of the element (210, e.g., main body) of the mobile vessel. According to some exemplary embodiments, the elements (210) and (220) of the mobile vessel (e.g., 200 of FIG. 3) may include a tubular or cylindrical shape about the center axis C, or about a respective center axis. Also shown in FIG. 4A is a direction of the local fluid velocity vector $V_{Fk}$ which in the exemplary configuration of FIG. 4A is assumed (substantially) parallel to an axial direction of the lateral portion of the well, as also shown in FIG. 3.

According to an embodiment of the present disclosure, the composition sensor (250) of FIG. 4A comprises two opposing arms (pair of opposing arms 250a, 250'a, oppositely arranged) rigidly coupled to one another via a base element (250c). According to an exemplary embodiment of the present disclosure and as shown in FIG. 4A, an axis of symmetry, S, of the two arms (250a, 250'a) coupled to the base element (250c) may pass through the center axis, C. In other words, the axis of symmetry, S, may be radial to the center axis, C. However, such radial configuration should not be considered as limiting the scope of the present disclosure as other non-radial configurations may be envisioned. A distance between the two arms (250a, 250'a) is configured to provide a measurement flow channel (250d) through which the fluid mixture can pass. As can be seen in FIG. 4A, an emission (illumination) aperture (2505a) for emitting different emission wavelength bands into the measurement flow channel (250d) is provided at a surface of the arm (250a). Furthermore, a collection aperture (250'a) for collecting attenuated versions of the emitted wavelengths bands through the measurement flow channel (250d) is provided at a surface of the arm (250'a). Further details of elements of the composition sensor (250) that interact with the apertures (2505a) and (2505'a) are provided, for example, with reference to FIG. 5 and FIG. 6A later described.

According to an embodiment of the present disclosure, the arms (250a, 250'a) may be configured to translate in a direction parallel to the axis of symmetry, S, as to allow sensing of the (local) composition at different radial positions. Such translation may be separate from, or concurrent with, a translation of the base element (250c). In some cases, it may be advantageous to measure the local composition at different angular positions about the center axis C of the element (220) for derivation of an angular profile of the composition. It follows that according to an exemplary embodiment of the present disclosure and as shown in FIG. 4B, the composition sensor (250), and therefore elements (250a, 250'a, 250c) thereof, may rotate about the center axis C of the element (220). For example, FIG. 4B shows the axis of symmetry, S, of the composition sensor (250) at an angular position that is different by an angle θ from the angular position of the axis of symmetry, S, of the composition sensor (250) shown in FIG. 4A. Such rotation of the composition sensor (250) about the center axis C may be considered as a rotation in the azimuth direction of the lateral portion of the well which therefore allows derivation of azimuthal profiles of the composition.

With continued reference to FIG. 4B, according to an exemplary embodiment of the present disclosure, the rotation of the composition sensor (250) may be based on a rotation of the element (220) to which the composition sensor (250) is rigidly coupled. In such configuration, the element (220), which may be referred to as a nose of the mobile vessel (200 of FIG. 3), may be a rotating part of the mobile vessel. Rotation of the nose (220) may be dependent or independent from a rotation of the vessel itself (i.e., 210 and 220 rotating in unison). The nose (220) may rotate clockwise and/or counterclockwise to achieve a desired angular position of the composition sensor (250). According to an exemplary embodiment of the present disclosure, the rotation of the composition sensor (250) may be based on rotation of the arms (250a, 250'a) while the base element (250c) remains fixed.

Figure 4C:
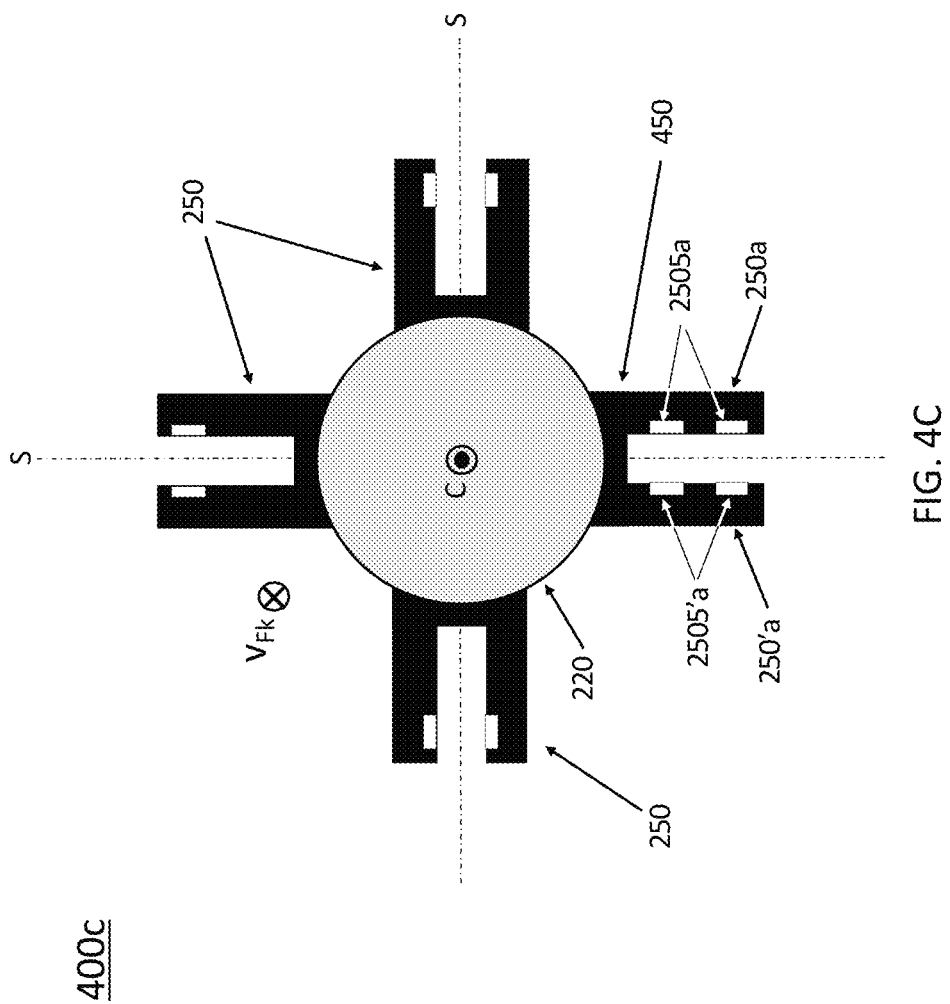
FIG. 4C shows a front view of a mobile vessel comprising a plurality of composition sensors according to the present disclosure.

FIG. 4C shows a configuration (400c) according to the present disclosure wherein a plurality (e.g., four) of composition sensors (250, 450) are attached to the element (220) of the mobile vessel (200) shown in FIG. 3. Accordingly, the configuration (400c) may allow simultaneous measurement of composition at a plurality of angular positions. Measurement of the composition at each of the plurality of angular positions may be provided by a composition sensor (250) similar to the composition sensor (250) described above with reference to FIGS. 4A and 4B, or, in some cases, a variant (450) of the composition sensor (250) that includes more than one emission and/or collection apertures. As can be seen in FIG. 4C, the axis of symmetry, S, of each of the composition sensors (250, 450) is positioned (e.g., fixed) at a different angular position. Although the exemplary configuration of FIG. 4C shows four composition sensors (250) arranged in quadrature, other configurations including more or less composition sensors (250) arranged at different angular positions may be envisioned. The configuration shown in FIG. 4C may allow simultaneous measurement of composition, or relative concentrations of fluid mixtures, at a plurality of angular positions without requiring any of the composition sensors (250) or respective arms (e.g., 250a, 250'a of FIG. 4A) to rotate about the center axis C. If desired, more flexibility (e.g., more angular data points) in measurement may be provided by rotating the composition sensors (250) or respective arms in a fashion similar to one described above with reference to FIG. 4B.

As shown in FIG. 4C, the composition sensor (450) according to the present teachings may include more than one emission aperture (2505a) in the arm (250a) and/or more than one collection aperture (2505'a) in the arm (250'a). Such configuration may allow, for example: i) composition measurement at different radial positions along the extension of the arms (250a, 250'a), ii) emission of different wavelength bands at different emissions apertures (2505*a*), or iii) collection at multiple apertures (2505'*a*) positioned at different locations with respect to a single emission aperture (2505*a*).

Figure 5:
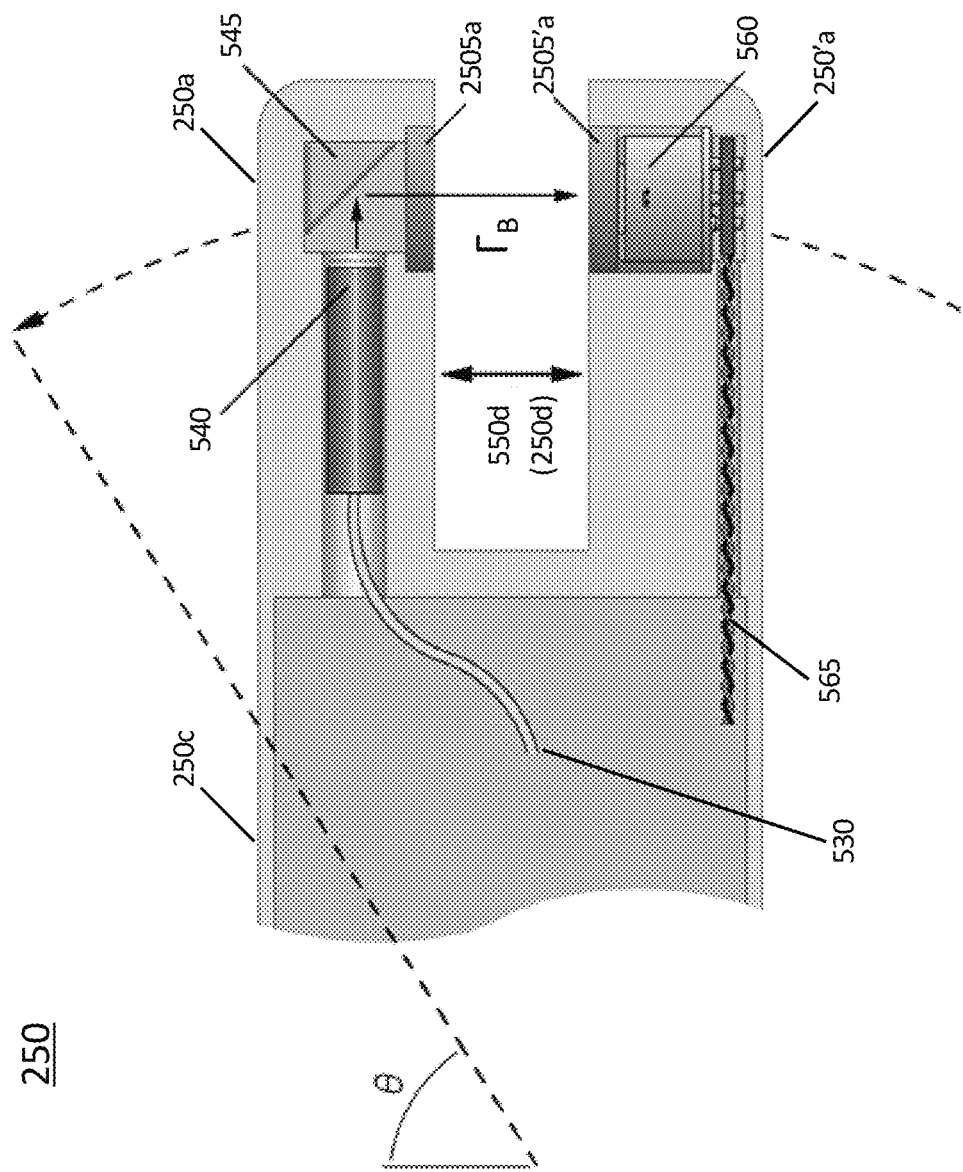
FIG. 5 shows a cross sectional view of the composition sensor according to an embodiment of the present disclosure.

FIG. 5 shows a cross sectional view of the composition sensor (250) according to an embodiment of the present disclosure, including details of constituent elements (e.g., 530, 540, 545, 560, 565) that interact with the emission aperture (2505*a*) and the collection aperture (2505'*a*). As shown in FIG. 5, (a signal with) a composite emission wavelength band, $\Gamma_B$, formed, for example, by the combination of emission bands from individual emitters, emitted at the emission aperture (2505*a*) is provided through an optical fiber (530) that is optically coupled to a collimator (540) and reflected at a mirror (e.g., steering mirror, prism, right angle mirror, 545) to exit the arm (250*a*) of the composition sensor (250) through the emission aperture (2505*a*). Upon exiting through the emission aperture (2505*a*), the emission wavelength band, $\Gamma_B$, traverses a length (550*d*) of the measurement flow channel (250*d*) and enters the arm (250'*a*) of the composition sensor (250) through the collection aperture (2505'*a*), and is collected by a light sensor (e.g., photosensor, photodetector, optical sensor/detector 560) that is sensitive to the emission wavelength band, FB. In turn, a portion of the emission wavelength band, $\Gamma_B$, collected by the light sensor (560) is transduced to an electrical signal that is routed via one or more wire conductors (565) to an electronic circuit (e.g., control electronics, not shown) for processing. Such portion of the emission wavelength band, $\Gamma_B$, may be based on absorption characteristics (e.g., absorption wavelength bands) in the emission wavelength band of the fluid mixture during the traversing of the measurement flow channel (250*d*). It should be noted that the light sensor (560) may be a single element light sensor that includes a single sensing surface, or may be a multi-pixel imaging array capable of resolving spatial distribution of the fluids in the mixture across the measurement flow channel (250*d*). A person skilled in the art would appreciate absence of any spectral filtering at the collection side of the composition sensor which therefore allows for increased (optical power) detection efficiency when compared to the prior art sensor described above. Because at any given time during operation of the sensor according to the present teachings the emitted signal includes an optical power that is concentrated within a target spectral (i.e., wavelength) band, all of the optical power of the emitted signal contributes to useful signal for probing/measuring the transmission/absorption of the fluid mixture at the target spectral band.

With continued reference to FIG. 5, according to an exemplary embodiment of the present disclosure, the collimator (540), the mirror (545) and a portion of the optical fiber (530) may be contained within an internal space (e.g., volume, housing) of the arm ((250*a*), and the light sensor (560) and portion of the wire conductors (565) may be contained within an internal space of the arm (250'*a*). According to an exemplary embodiment, relative arrangements of the mirror (545), the apertures (2505*a*, 2505'*a*) and the light sensor (560) may be such as to provide an optical axis for the emitted signal that is substantially normal to respective surfaces of the apertures (2505*a*, 2505'*a*) and the light sensor (560). According to an exemplary embodiment of the present disclosure, the apertures (2505*a*, 2505'*a*) may be windows fabricated from sapphire. A person skilled in the art would appreciate that transparency of sapphire in the near infrared spectrum, as well as its hardness and toughness, make the sapphire suitable for operation of the composition sensor according to the present disclosure in harsh environments, including in a lateral section of an oil well (e.g., Well_1 of FIG. 1).

FIG. 6A shows an optical layout (600) of the composition sensor (250) according to the present disclosure, including a plurality of emission (light) sources (e.g., three, A, B, C) optically coupled via respective optical fibers (630A, 630B, 630C) to a wavelength multiplexer (e.g., wavelength-division multiplexer, 620), the wavelength multiplexer (620) coupled to the optical fiber (530) described above with reference to FIG. 5. For clarity, only the emission and collection apertures (2505*a*, 2505'*a*) of the composition sensor (250) distanced by the length (550*d*) of the measurement flow channel (250*d*) are shown in the optical layout (600). It should be noted that the composition sensor according to the present disclosure may include at least two emission sources emitting different emission wavelength bands, therefore the exemplary configuration including three emission sources (A, B, C) of FIG. 6A emitting different emission wavelength bands should not be considered at limiting the scope of the present disclosure. As known to a person skilled in the art, the wavelength multiplexer (620) is a passive element that combines emissions of a plurality of sources (e.g., A, B, C, etc.) provided at a plurality of input fibers (e.g., 630*a*, 630*b*, 630*c* of FIG. 6A) of the multiplexer into one single-mode fiber output (e.g., 530 of FIG. 6A).

With continued reference to FIG. 6A, the wavelength multiplexer (620) may multiplex light emitted from each of the emission sources (A, B, C) into the optical fiber (530) for emission through the aperture (2505*a*). In a configuration that includes more than one composition sensor or more than one set of emission and/or collection apertures (e.g., 250 and 450 of FIG. 4C), the wavelength multiplexer (620) may further couple (e.g., split) light from the emission sources (A, B, C) to respective optical fibers (e.g., 530' of FIG. 6A) of additional composition sensor(s) and/or emission apertures. According to an exemplary embodiment of the present disclosure, an optical splitter may be combined with (e.g., at an output of) the wavelength multiplexer (620) to split the multiplexed emission into substantially equal power emissions coupled to the respective optical fibers (e.g., 530, 530') of multiple composition sensors and/or emission apertures.

According to an embodiment of the present disclosure, each of the emission sources (A, B, C) may be configured to emit a high-brightness and spectrally narrow light in the near infrared spectrum. As used herein, the expression "spectrally narrow" refers to a spectral content at full-width at half-maximum bandwidth in a wavelength range from 20 to 100 nm. According to an exemplary embodiment, such characteristics of the emission sources (A, B, C) may be provided by a near infrared superluminescent light emitting diode (NIR SLED) known to a person skilled in the art. In some implementations, each of the emission sources (A, B, C) and the respective optical fibers (630A, 630B, 630C) can be provided by a readily available pre-packaged assembly. Such pre-packaged assemblies may allow simplification of the optical path, such as, for example, removal of one or more of the elements (540, 545) shown in FIG. 5.

FIG. 6B show graphs representative of emission spectra of exemplary superluminescent light emitting diodes (SLEDs) that may be used as the emission sources (A, B, C) in the optical layout (600) of FIG. 6A. As shown in FIG. 6B, the emission spectrum of the emission source A may consist of an emission wavelength (spectral) band concentrated at a center wavelength of about 1480 nm, the emission spectrum of the emission source B may consist of an emission wavelength (spectral) band concentrated at a center wavelength of about 1620 nm, and the emission spectrum of the emission source C may consist of an emission wavelength (spectral) band concentrated at a center wavelength of about 1680 nm. According to an exemplary embodiment of the present disclosure, the emission spectra (i.e., wavelength bands) shown in FIG. 6B may correspond to a composition sensor according to the present disclosure for measuring relative concentrations of oil, gas and water in a fluid mixture at a downhole of an oil well. In particular, as later described with reference to, for example, FIGS. 7A and 7B, the emission wavelength bands may be selected to target (known) one or more absorption wavelength bands of oil, gas, or water. For example, the emission spectrum of the emission source A may target an absorption wavelength band of water and the emission spectrum of the emission source C may target absorption wavelength bands of oil and/or gas. On the other hand, the emission spectrum of the emission source B may target an absorption wavelength band outside of absorption wavelength bands of water, oil, and gas, which may be used as a reference absorption data point of the fluid mixture that may be considered as being (substantially) invariant/insensitive with respect to concentrations of any of the target fluids (oil, gas, water).

FIG. 6C show graphs representative of emission spectra of the SLEDs of FIG. 6B through the wavelength multiplexer (620) of FIG. 6A. As can be seen in FIG. 6C and when comparing to the graphs of FIG. 6B, the wavelength multiplexer (620) may further reduce a bandwidth of the emission wavelength bands (e.g., A, B, C) while maintaining a same center wavelength and a (substantially) same emission power/intensity. Therefore, the wavelength multiplexer (620 of FIG. 6A) may further shape each of the emission wavelength bands to obtain a respective spectrally narrow content at full-width at half-maximum bandwidth in a wavelength range from 10 to 100 nm. It should be noted that although FIG. 6C shows the emission spectra (e.g., A, B, C) as superimposed, at any given time during a measurement via the composition sensor according to the present disclosure, only one of the emission wavelength bands (e.g., A, B, C) is output by the wavelength multiplexer (e.g., 620 of FIG. 6A) for emission through the length of measurement flow channel (e.g., 550d of FIG. 6A).

It is noted that a consequence of using the spectrally narrow emission sources according to the present disclosure (e.g., per FIGS. 6B, 6C), for a given (optical) input power, a higher signal-to-noise ratio at the optical detector (e.g., 560 of FIG. 5) can be obtained when comparing, for example, to the above described prior art sensor using a broadband emission source. As a consequence, increased optical power in a given spectral band can be obtained, which can therefore enable a shorter integration time of a signal detected by the optical detector to achieve an equivalent signal-to-noise performance, which in turn can enable a higher measurement cadence of the composition sensor of the present teachings for an equivalent input power (when comparing to the prior art sensor). In other words, in order to obtain a performance equivalent to one of the present composition sensor, the spectrally broad emission source used in the prior art sensor must be operated with higher input power to achieve equivalent spectral brightness (optical power per unit wavelength) and/or a single measurement must be collected over a longer integration time due to lower optical throughput within a given spectral band to achieve an equivalent signal-to-noise ratio. It should be noted that the (relatively) longer measurement times required by the prior art sensor may be undesirable in applications where a flowing mixture of fluids (e.g., downhole of an oil well) is being analyzed, since the composition in the sampling region may change over the duration of a single measurement.

FIG. 6D shows a graph representative of a time multiplexing scheme of emission sources used in the composition sensor according to the present teachings. The exemplary nonlimiting scheme shown in FIG. 6D assumes time multiplexing of three emission sources, such as, for example, the SLEDs (e.g., A, B, C) described above with reference to FIGS. 6A-6C. As shown in FIG. 6D, such time multiplexing scheme pulses (turns ON, activates) each of the emission sources (e.g., A, B, C) at different times. Furthermore, as shown in FIG. 6D, each emission source may be pulsed a number of consecutive times (e.g., 6 per FIG. 6D) before a next emission is pulsed (turned ON, activated). Control electronics of the composition sensor (e.g., 250 of FIG. 5) may be used to synchronize a detected/transduced electrical signal by the optical detector (e.g., 560 of FIG. 5) with an activated emission source.

As shown in FIG. 6D and according to an exemplary nonlimiting embodiment of the present disclosure, the time multiplexing scheme may include a same number of pulses (e.g., n=6) emitted at a same frequency ($f_p$) for each of the emission sources (e.g., A, B, C). Accordingly, a maximum cadence/repetition rate for a complete measurement cycle of a corresponding composite sensor may be provided at a frequency $f_p=(1/k)*f_p$, wherein k=p×n, and p is a number of time multiplexed emission sources (e.g., p=3 in FIG. 6D). It should be noted that the multiplexing scheme according to the present disclosure may be based on any combination of values of n>1 and p>1. Furthermore, the frequency $f_p$ may be such as to provide an ON-time of a pulse (e.g., $\sim 1/f_p$) in a range from seconds to nanoseconds. Pulses at higher frequencies ($f_p$) may be used in applications where frequency lock-in amplification of the detected optical signal is desired. A person skilled in the art would clearly understand the benefits of the frequency lock-in amplification in cases where higher signal-to-noise ratios are desired in presence of, for example, noise from interfering/local light. In such cases, the higher frequencies ($f_p$) may be in a range from 10 Hz to 10 GHz.

FIG. 7A shows a graph representative of a wavelength absorption bands of (liquid) water that, for example, may be present in a downhole of an oil well. As can be seen in FIG. 7A, in the infrared region of the spectrum, water includes a first wavelength absorption band, W1, (having a peak) that is centered at a wavelength of about 1450 nm, and a second wavelength absorption band, W2, (having a peak) that is centered at a wavelength of about 1950 nm. As shown in FIG. 7A, peak absorption, as provided for example by an absorption coefficient, for the second wavelength absorption band, W2, is substantially higher than the peak absorption for the first wavelength absorption band, W1 (e.g., 140/cm versus 35/cm).

Teachings according to the present disclosure avoid operation of the composition sensor at wavelengths greater than 1800 nm because the optical absorption due to liquid water near 1950 nm is strong enough to attenuate light by greater than 99.9% over a propagation distance (i.e., 550d of FIG. 6A) of 1 mm or more. In other words, an emitted light with an emission wavelength band at, or close to, 1950 nm, would be mostly absorbed by the water component of the fluid mixture through such propagation distance of 1 mm or more, and therefore practically no signal in the emission wavelength band may be detected by the light detector (e.g., 560 of FIG. 5).

It follows that according to an embodiment of the present disclosure, the composition sensor (e.g., 250 of FIG. 5) of the present teachings may target the first wavelength absorption band, W1, of the liquid water as an indication of a water concentration in a measurement of the composition of the fluid mixture. This allows for an increased length (550*d* of FIG. 5) of the measurement flow channel (250*d* of FIG. 5) and thereby further immune measurement accuracy of the present composition sensor by allowing unimpeded flow of multi-phase mixtures, particularly when at least one of the components of a mixture has a high enough viscosity. According to an exemplary embodiment of the present disclosure, such increased length may be several millimeters and close to 1 cm, such as, for example, in a range from 1 mm to 10 mm, such as for example, from 2 mm to 5 mm.

FIG. 7B show graphs representative of exemplary wavelength emission bands of the composition sensor according to the present disclosure, and wavelength absorption bands of components of an oil well mixture. In addition to the wavelength emission bands of the emission sources (e.g., A, B, C) and the wavelength absorption band, W1, of liquid water described above with reference to FIGS. 6B and 7A, FIG. 7B further includes wavelength absorption bands of methane (gas) and crude oil (liquid) that may be present in a downhole of an oil well. As can be seen in FIG. 7B, the absorption band of methane includes a peak region in a spectrum range from about 1640 nm to about 1720 nm, and the absorption band of crude oil includes a peak region in a spectrum range from about 1680 nm to about 1800 nm. Accordingly, as can be seen in FIG. 7B, the target absorption bands considered in the present composition sensor for measuring downhole composition, may range from 1400 nm to 1800 nm.

With continued reference to FIG. 7B, the wavelength emission band A may target the wavelength absorption band, W1, of water, the wavelength emission band C may target the wavelength absorption band of methane, and the wavelength emission band C may target the wavelength absorption band of crude oil. By having a wavelength emission band that overlaps a wavelength absorption band of a target component of a fluid mixture, an emitted light through the measurement channel of the present composition sensor may be absorbed proportionally to a concentration of the target component. In other words, the wavelength emission band A overlapping the wavelength absorption band W1 may be used to detect concentration of water, the wavelength emission band B overlapping the wavelength absorption band of methane may be used to detect concentration of methane, and the wavelength emission band C overlapping the wavelength absorption band of crude oil may be used to detect concentration of crude oil. It should be noted that actual wavelengths bands emitted through the emission aperture (e.g., 2505*a* of FIG. 6A) may be narrower than the emission wavelength bands shown in FIG. 7B due to the multiplexing described above with reference to FIGS. 6A-6C.

With continued reference to FIG. 7B, actual derivation of relative concentrations of mixtures in the fluid may be based on ratiometric values of absorptions sensed in the different target absorption bands. By considering ratios of the sensed absorptions, noise effects in the sensor that may equally affect all wavelength bands can be eliminated.

FIGS. 8A, 8B and 8C show graphs representative of attenuation of each of the emission wavelength bands (A, B, C) at different wavelengths absorption bands (e.g., water, crude oil, methane) of a fluid mixture at a downhole of an oil well as a function of a length of the measurement flow channel (e.g., propagation length, 550*d* of FIG. 6A). Such graphs may be used to determine an upper limit for the length of the measurement flow channel, the upper limit allowing to achieve benefits of a greater length as described above with reference, for example, to FIG. 7A. As can be seen in the graphs of FIGS. 8A-8C, a variation of water concentration may be observed for a (propagation) length of up to about 5 mm at the emission wavelength bands B and C, and up to about 1.5 mm at the emission wavelength band A. In other words, considering a length of the measurement flow channel equal to 5 mm, then even if sensing at the emission wavelength band A is insensitive (e.g., saturated at bottom of sensor, no light detected) with respect to a concentration of water, sensing at the emission wavelengths B and C are sensitive with respect to a concentration of water and may therefore be used, alone or in combination, to derive a measurement for concentration of water. Similarly, considering the 5 mm length, each of the methane and crude oil concentrations may be measured via sensing through at least one of the available emission wavelength bands (e.g., A, B, C) for single measurement data point, or through two of the available wavelength bands by combining two measurement data points.

FIG. 9 show stratified components of a pipe in a lateral section of an oil well mixture for different flow conditions (e.g., identified as (a)-(d)) of the mixture, the different flow conditions comprising pressure, volume fraction and fluid velocity. As shown in FIG. 9, the stratified (e.g., layered) components may include, in order from the bottom of the pipe (cross section of the pipe shown), sand that is at the bottom of the pipe (e.g. lateral section), liquid water that is heavier than oil and gas, oil that is heavier than oil (e.g., crude oil), and gas (e.g., methane). Such flow conditions, representative of typical flow conditions in a lateral section of an oil well, and verified by Applicant through modeling, show that phase separation between the different components of the mixture may exist, and which may therefore allow a single-phase measurement at different angular positions of the composition sensor (e.g., FIGS. 4B and 4C). In turn, this may allow determination of height of each of the stratified components by gradual/incremental rotation of the angular position.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only and is not intended to be limiting. As used in this specification and the appended claims, the singular forms "a,"

"an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A system for gathering information about physical properties of a fluid mixture in a lateral section of an oil-gas producing well, the system comprising:
a mobile vessel configured for submersion in the fluid mixture of the lateral section of the oil-gas producing well, the fluid mixture comprising water, methane and crude oil; and
a composition sensor attached to the mobile vessel, the composition sensor comprising:
a pair of opposing arms separated by a distance that defines a length of a measurement flow channel of the composition sensor through which measurement flow channel the fluid mixture can pass;
an emission aperture and a collection aperture oppositely arranged in the pair of opposing arms and having respective oppositely arranged surfaces separated by said distance and in contact with the fluid mixture upon passing of the fluid mixture through the measurement flow channel; and
a plurality of spectrally narrow emission sources having respective plurality of emission wavelength bands in an infrared wavelength region between 1400 nm to 1800 nm,
wherein the lateral section of the oil-gas producing well comprises a plurality of perforated production zones for provision of a combined inflow of the fluid mixture,
wherein the mobile vessel is further configured for positioning near each perforated production zone of the plurality of perforated production zones for measurement of a respective inflow contribution to the combined inflow of the fluid mixture, the respective inflow contribution based on relative concentrations of the water, methane and crude oil of the fluid mixture measured by the composition sensor near the each production zone,
wherein the plurality of emission wavelength bands includes three emission wavelength bands that overlap absorption wavelength bands of the water, methane and crude oil of the fluid mixture, and
wherein the composition sensor is configured to emit the plurality of emission wavelength bands through the emission aperture according to a time multiplexing scheme for measurement of the relative concentrations of the water, methane and crude oil.

2. The system according to claim 1, wherein:
the composition sensor further comprises a wavelength multiplexer configured to couple the plurality of emission wavelength bands into a single optical fiber for emission through the emission aperture.

3. The system according to claim 2, wherein:
the single optical fiber is optically coupled to the emission aperture through one or more of: a) a collimator; or b) a mirror, arranged proximate the emission aperture in an internal space of the pair of opposing arms.

4. The system according to claim 1, wherein:
each of the plurality of spectrally narrow emission sources is a superluminescent light emitting diode (SLED).

5. The system according to claim 1, wherein:
each of the plurality of emission wavelength bands has a spectral content at full-width at half-maximum bandwidth in a wavelength range from 10 nm to 100 nm.

6. The system according to claim 1, wherein:
a first emission wavelength band of the plurality of emission wavelength bands overlaps an absorption wavelength band of water that is centered at a wavelength of about 1450 nm.

7. The system according to claim 6, wherein:
the first emission wavelength band is centered at a wavelength of about 1480 nm.

8. The system according to claim 6, wherein:
a second emission wavelength band of the plurality of emission wavelength bands overlaps an absorption wavelength band of methane that is in a range from about 1640 nm to about 1720 nm.

9. The system according to claim 8, wherein:
the second emission wavelength band is centered at a wavelength of about 1620 nm.

10. The system according to claim 8, wherein:
a third emission wavelength band of the plurality of emission wavelength bands overlaps an absorption wavelength band of crude oil that is in a range from about 1680 nm to about 1800 nm.

11. The system according to claim 10, wherein:
the third emission wavelength band is centered at a wavelength of about 1680 nm.

12. The system according to claim 1, wherein:
the length of the measurement flow channel is in a range from 1 mm to 10 mm.

13. The system according to claim 1, wherein:
the composition sensor further comprises a photosensor arranged proximate the collection aperture in an internal space of the pair of opposing arms, the photosensor configured to sense a time multiplexed emitted wavelength band of the plurality of emission wavelength bands collected through the collection aperture.

14. The system according to claim 13, wherein:
the composition sensor is a multi-pixel imaging array.

15. The system according to claim 1, wherein:
the time multiplexing scheme is configured to emit a plurality of consecutive pulses of a same emission wavelength band at a frequency in a range from 10 Hz to 10 GHz.

16. The system according to claim 1, wherein:
the mobile vessel comprises a first element having a tubular shape about a center axis of the first element, and
the pair of opposing arms of the composition sensor are rigidly attached to the first element.

17. The system according to claim 16, wherein:
the first element is configured to rotate about the center axis.

18. The system according to claim 16, wherein:
the pair of opposing arms are arranged in parallel, one opposite the other with respect to an axis of symmetry of the pair of opposing arms, and
said axis of symmetry is radial to the center axis.

19. The system according to claim 18, wherein:
the composition sensor further comprises:
an additional pair of opposing arms separated by the length of the measurement flow channel of the composition sensor; and
an additional emission aperture and an additional collection aperture oppositely arranged in the additional pair of opposing arms;

wherein the composition sensor is configured to emit the plurality of emission wavelength bands through the emission aperture and the additional emission aperture according to the time multiplexing scheme.

20. The system according to claim 19, wherein:

wherein an axis of symmetry of the additional pair of opposing arms is radial to the center axis, and wherein the axis of symmetry of the pair of opposing arms and the axis of symmetry of the additional pair of opposing arms are at different angular positions about the center axis.

* * * * *